United States Patent [19]

Rogasch

[11] Patent Number: 5,015,093
[45] Date of Patent: May 14, 1991

[54] ELECTROMAGNET FOR AN ATOMIC ABSORPTION SPECTROMETER

[76] Inventor: Klaus P. Rogasch, Th.-Hofmannweg 3, D-7772 Uhldingen Muhlhofen 1, Fed. Rep. of Germany

[21] Appl. No.: 435,431

[22] Filed: Nov. 7, 1989

[30] Foreign Application Priority Data

Mar. 18, 1988 [DE] Fed. Rep. of Germany ....... 3809215

[51] Int. Cl.$^5$ ...................... G01N 21/31; G01N 21/74
[52] U.S. Cl. ..................................... 356/307; 356/312
[58] Field of Search ................ 356/307, 315, 312, 319

[56] References Cited

U.S. PATENT DOCUMENTS

| 4,035,083 | 7/1977 | Woodriff et al. | 356/307 |
| 4,407,582 | 10/1983 | Woodriff | 356/312 |
| 4,449,820 | 5/1984 | Koizumi et al. | 356/307 |

FOREIGN PATENT DOCUMENTS

| 1964469 | 10/1973 | Fed. Rep. of Germany . |
| 2148783 | 5/1974 | Fed. Rep. of Germany . |
| 2314207 | 11/1979 | Fed. Rep. of Germany . |
| 2165106 | 2/1984 | Fed. Rep. of Germany . |
| 3534417 | 4/1987 | Fed. Rep. of Germany . |

OTHER PUBLICATIONS

Frech et al., *Analytical Chemistry*, vol. 58, No. 9, Aug. 1986, pp. 1973–1977.
Violi, *Bulletin Oerlikon*, No. 385/386, Jan. 1969, pp. 1–4.
Liddell et al., *Analytical Chemistry*, vol. 52, No. 8, Jul. 1980, pp. 1256–1260.
Tie-Zheng et al., *Analytical Chemistry*, vol. 57, No. 2, Feb. 1985, pp. 424–427.
Sukhorukov et al., *Instruments & Experimental Techniques*, No. 5, Part 2, Sep.–Oct. 1986, pp. 1224–1225.

*Primary Examiner*—F. L. Evans
*Attorney, Agent, or Firm*—Thomas P. Murphy; Edwin T. Grimes

[57] ABSTRACT

A solenoid serves for generating a magnetic field at the location of a sample which is to be atomized in an atomic absorption spectrometer. A shift of the absorption lines of the atoms in a sample relatively to the emission lines in a measuring light beam (18) passed through the atomized sample is effected by the magnetic field due to the Zeeman effect. The solenoid (44) comprises a pair of pole pieces (46, 48) between which an air gap is formed. An atomizing device atomizes the sample within this air gap. Field coils generate a magnetic flux through the pole pieces (46, 48), the air gap and a magnetic return path (76). The field coils (60, 62) are arranged on pole pieces (46, 48) close to the air gap. The windings of the field coils (60, 62) are formed by tubes (216) which are designed to permit passage of a cooling liquid therethrough.

9 Claims, 3 Drawing Sheets

ELECTROMAGNET FOR AN ATOMIC ABSORPTION SPECTROMETER

TECHNICAL FIELD

The invention relates to a solenoid for generating a magnetic field at the location of the sample in an atomic absorption spectrometer wherein a shift of the absorption lines of the atoms of the element looked for in the sample relative to the emission lines of this element in a measuring light beam passed through the atomized sample is caused by the magnetic field due to the Zeeman effect, comprising (a) a pair of pole pieces between which an air gap is formed, an atomizing device atomizing the sample within this air gap, (b) a magnetic return path connecting the pole pieces, (c) field coils for generating a magnetic flux through the pole pieces, the air gap and the magnetic return path.

Atomic absorption spectrometers serve for determining the amount or concentration of an element looked for in a sample. For this purpose a measuring light beam from a line emitting light source, a hollow cathode lamp for example, is directed to a photo-electrical detector. An atomizing device is arranged in the path of rays of this measuring light beam. The sample which is to be analyzed is atomized in this atomizing device such that the components of the sample are present in an atomic state. The measuring light beam contains the resonant lines of the element looked for. These resonant lines of the measuring light beam are absorbed by the atoms of the element looked for in the cloud of atoms, while ideally the other elements contained in the sample do not influence the measuring light beam. Therefore the measuring light beam is subjected to an attenuation which is a measure of the number of the atoms looked for in the path of the measuring light beam and thus a measure of the concentration or the amount of the looked-for element in the sample, depending on the method of atomization applied. The absorption to which the measuring light beam is subjected is caused not only by the atoms of the element looked for. There is a "background absorption" due to the absorption of the light by molecules for example. This background absorption has to be compensated for when making particularly highly sensitive measurements.

A flame may serve as atomizing device into which a sample is sprayed an as a solution. For highly sensitive measurements the electrothermal atomization is preferably used: The sample is introduced into a furnace which is heated to high temperature by passing electrical current therethrough. Thereby the sample is first dried, then ashed thereafter atomized. Then a "cloud of atomes" is generated in the furnace in which cloud the atom looked for is present in an atomic state. The measuring light beam is passed through this furnace. These furnaces can have different shapes. Conventionally they are made of graphite.

The "Zeeman effect" is used for background compensation. When a magnetic field is applied to the absorbing atoms in the atomized sample, a splitting and shifting of the resonant lines of these atoms is effected. Then the resonant lines of the atoms no longer coincide with the spectral lines of the measuring light beam and no atomic absorption takes place in the borderline case. This permits discrimination between non-atomic background absorption which is also present when the magnetic field is applied, and real atomic absorption which is superposed on the background absorption when the magnetic field is not applied.

The invention relates to a solenoid which causes the Zeeman effect at the location of the sample in an atomic absorption spectrometer in order to measure the background absorption.

BACKGROUND ART

From German patent application No. 1,964,469 an atomic absorption spectrometer is known wherein the radiation originates from a single light source designed as a line emitter, the radiation of which passing through the sample is frequency modulated by use of the longitudinal Zeeman effect. In this prior atomic absorption spectrometer a hollow cathode lamp is arranged between the pole pieces of a solenoid. One of the pole pieces has a bore through which the measuring light beam passes. Then the measuring light beam is directed through a flame serving as an atomizing device and a monochromator and impinges upon a photo-electrical detector. The solenoid is arranged to be switched on and off, whereby the atomic absoption of the sample atoms compensated with respect to the background absorption can be determined from the difference of the signals with the solenoid switched off and switched on. The windings of the solenoid are provided on the pole pieces.

In this prior art atomic absorption spectrometer the emission lines of the line emitting light source are periodically shifted by the Zeeman effect and thus the emitted light frequency is modulated and not the absorption lines of the sample. This may cause problems when a hollow cathode lamp is used as light source because the discharge of the hollow cathode lamp is influenced by the magnetic field, as already mentioned in German patent application No. 1,964,469.

From German patent application No. 2,165,106 it is known to apply the magnetic field of a solenoid arranged to be switched on and off to the atomizing device, i.e. to the sample which is to be atomized, instead to the light source. Therein the atomizing device is a flame. The magnetic field is applied perpendicular to the direction of propagation of the measuring light beam. A splitting of the absorption lines due to the "transverse" Zeeman effect is effected, which again effects a relative shift of the emission lines of the measuring light beam and the absorption lines of the sample. Again it can be discriminated between atomic absorption by the atoms of the element looked for and non-specific background absorption by switching the magnetic field on and off.

When the transverse Zeeman effect is used a spectral line is split into a central line the wave length of which corresponds to the non-shifted wave length of the respective line with the magnetic field switched off and two side lines which relative thereto are shifted to longer and shorter wave lengths. The central line and the side lines are polarized differently. Therefore the influence of the central line can be eliminated by a polarizer.

Furnaces are known as atomizing devices for the electrothermal atomization of the sample. Graphite tubes serve for this purpose for example, which are held between annular contacts and through which the measuring light beam passes in longitudinal direction. A strong electrical current is passed through the annular contacts through the graphite tube. Thereby the sample introduced into the graphite tube is atomized and forms a "cloud of atoms" within the graphite tube. In this cloud of atoms the element looked for is present in atomic state. Such atomizing devices operating with a graphite tube are known from German patent application No. 23,14,207 and German patent application No. 21,48,783, for example.

It is also known to effect compensation of the background absorption by the Zeeman effect in such atomizing devices which operate with a graphite tube flown through by current in longitudinal direction. For this purpose a pulsating magnetic field directed transverse to the direction of propagation of the measuring light beam is applied to the graphite tube by a solenoid.

Furnaces for the electrothermal atomization of a sample in an atomic absorption spectrometer are known in which the current is not passed through a graphite tube in longitudinal direction but in circumferential direction. Examples for this are U.S. Pat. No. 4,407,582 and German patent application No. 35,34,417 as well as the publication in "Analytical Chemistry" 58 (1986), 1973 having substantially the same contents.

DISCLOSURE OF THE INVENTION

It is the object of the invention to design a solenoid of the above mentioned type such that a magnetic field which is as strong as possible is achieved at the location of the sample with a stray field being as small as possible and a solenoid having dimensions as small as possible.

According to the invention this object is achieved in that (d) the field coils are arranged on the pole pieces close to the air gap, and (e) the windings of the field coils are formed by tubes through which a cooling liquid can be passed.

The field coils are arranged on pole pieces. Thereby the stray field is reduced. Therefore a stronger magnetic field can be generated within the air gap with an electrical power given. Disadvantages of a strong stray field are avoided. The pole pieces can be arranged close to the atomizing device without causing undesired heating of the field coil, which is heated anyway by the exciting current, by the heat of the atomizing device, a furnace for the electrothermal atomization of the sample for example. On the contrary: The cooling liquid carries heat off. Arranging the pole pieces close to the atomizing device is as well effective in the sense of homogenizing the magnetic field and a reduction of the power required. The dimension of the solenoid can be smaller.

Further embodiments of the invention are subject matter of the sub-claims.

An embodiment of the invention will now be described in further detail with reference to the accompanying drawings.

PREFERRED EMBODIMENT OF THE INVENTION

Figure 1:
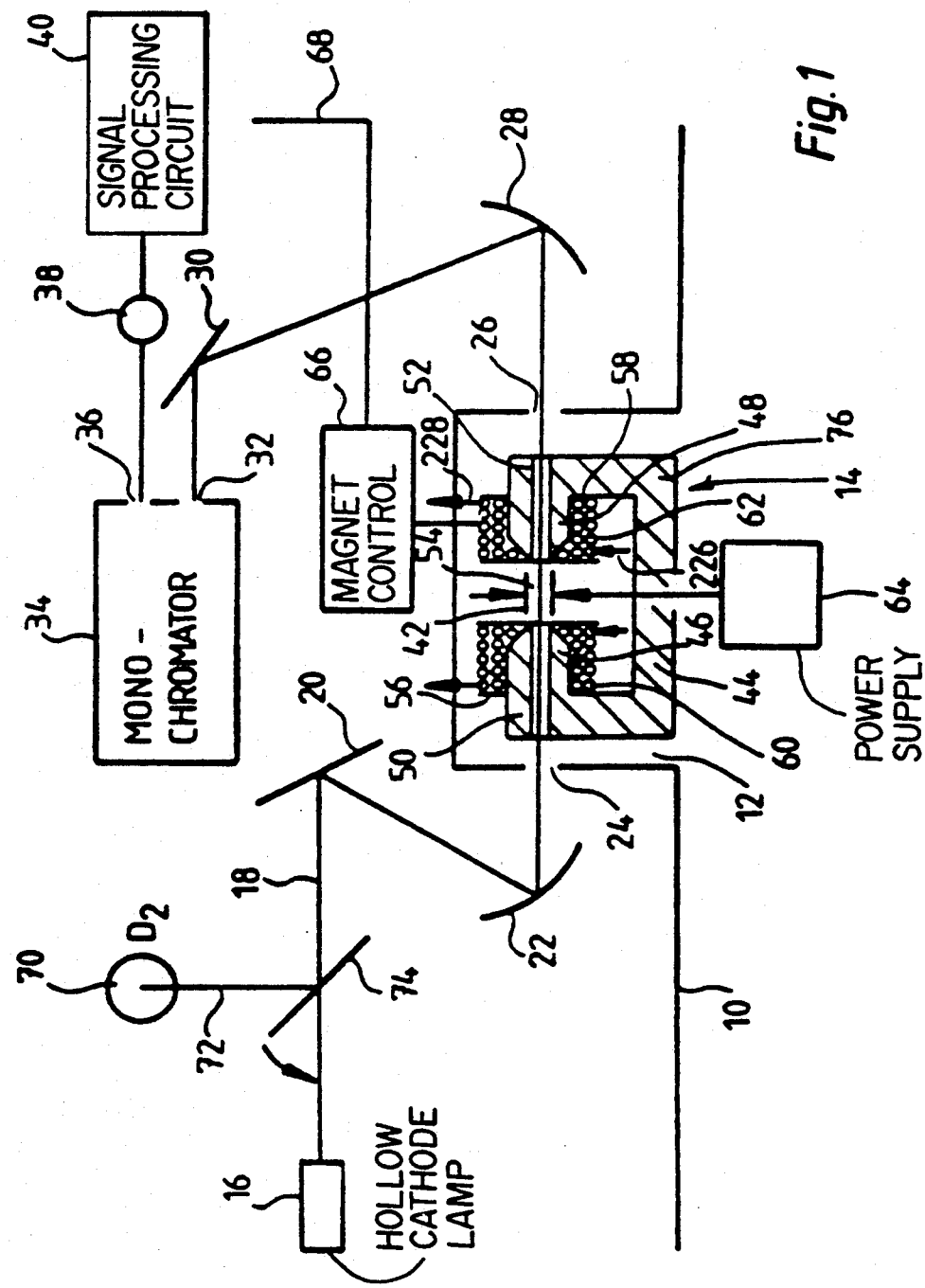
FIG. 1 shows shematically the construction of an atomic absorption spectrometer in which the background absorption is compensated by use of the longitudinal Zeeman effect.

The Figure shows a shematical illustration of the entire atomic absorption spectrometer.

The atomic absorption spectrometer has a housing 10 in which the lamps, the optical system and the photosensitive detector are arranged. The housing 10 defines a sample cavity 12. An atomizing device 14 is arranged in the sample cavity 12.

The atomic absorption spectrometer has a hollow cathode lamp as first light source 16. The light source 16 emits a line spectrum which corresponds to the resonant lines of a certain element looked for. A measuring light beam 18 originates from the light source 16. The measuring light beam 18 is deviated by a plane mirror 20 and collected in the center of the sample cavity by a concave mirror 22 through an opening 24 of the housing 10. Then the measuring light beam passes through an opening 26 of the housing 10 aligned with the opening 24 and impinges upon a second concave mirror 28. The second concave mirror 28 focusses the measuring light beam 18 through a plane mirror 30 on the inlet slit 32 of a monochromator 34. A photo-electrical detector 38 is arranged behind an outlet slit 36 of the monochromator 34. The signal of the photo-electrical detector 38 is supplied to a signal processing circuit 40.

The atomizing device 14 comprises a furnace for electrothermal atomization, only the actual furnace body 42 of the furnace device being illustrated in FIG. 1, and a solenoid 44 which is arranged to be switched on and off in order to generate a magnetic field at the location of the sample. The solenoid 44 has two aligned pole pieces 44 and 46 between which the furnace body 42 is arranged. Aligned bores 50 and 52 are provided in the pole pieces 46 and 48. The bores 50 and 52 are aligned with a longitudinal bore 54 of the furnace body 42. The measuring light beam 18 passes through the bores 50 and 52 and through the longitudinal bore of the furnace body. Coil holders 56 and 58, respectivily, are arranged on the pole pieces 50 and 52. Coils 60 and 62, respectively, of the solenoid 44 are wound on these coil holders 56 and 58. Numeral 64 designates a power unit which controls the current through the furnace body 42. As indicated the current is supplied transversely to the direction of the measuring light beam 18 and flows through the tubular furnace body 42 in circumferential direction. The solenoid 44 is controlled by a magnet control 66 such that the magnetic field alternately is switched on and off. At the location of the sample the magnetic field of the solenoid 44 is directed within the furnace body in the direction of propagation of the measuring light beam 18. Therefore the longitudinal Zeeman effect is generated at the sample atoms when the magnetic field is switched on. That means that the absorption lines of the sample atoms are split into two lines, each, which are shifted relative to the undisturbed original absorption line. There is no atomic absorption in the sample at the wave length of the original absorption line. Therefore also the atoms of the elements looked for do not absorb the measuring light beam 18 because this measuring light beam contains only the non-shifted resonant lines which are characteristic for the element. Therefore only the background absorption is measured when the magnetic field is switched on. The component of real atomic absorption corrected with respect to the background absorption can be determined from the measurements with the magnetic field switched on and off. For this purpose the cycle of switching the solenoid 44 on and off is supplied to the signal evaluation circuit 40 as indicated by a line 68.

Figure 2:
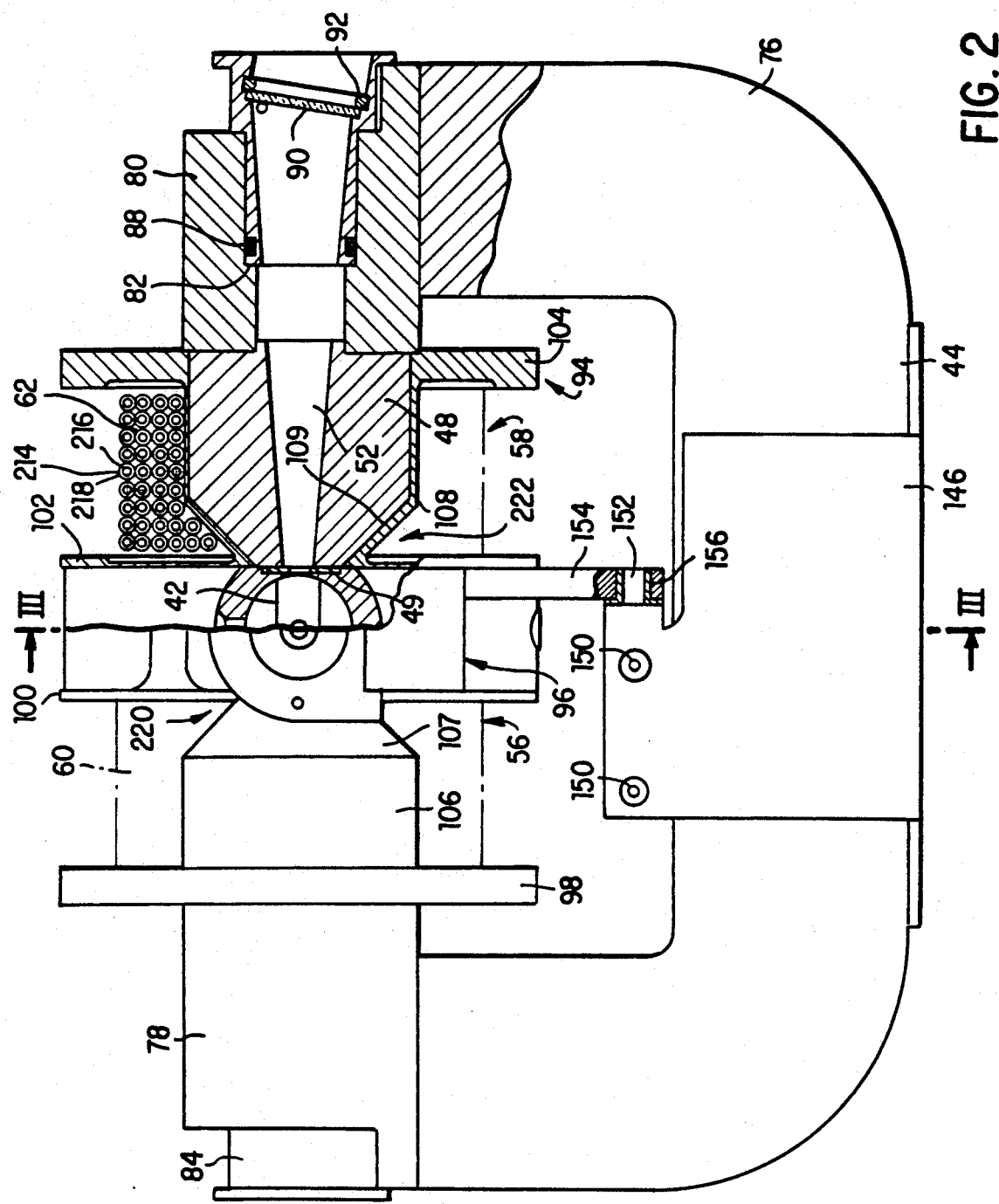
FIG. 2 shows a partially sectional side elevation of the solenoid by which the longitudinal Zeeman effect is generated and a furnace for the electrothermal atomization of a sample in the air gap of the solenoid.
Figure 3:
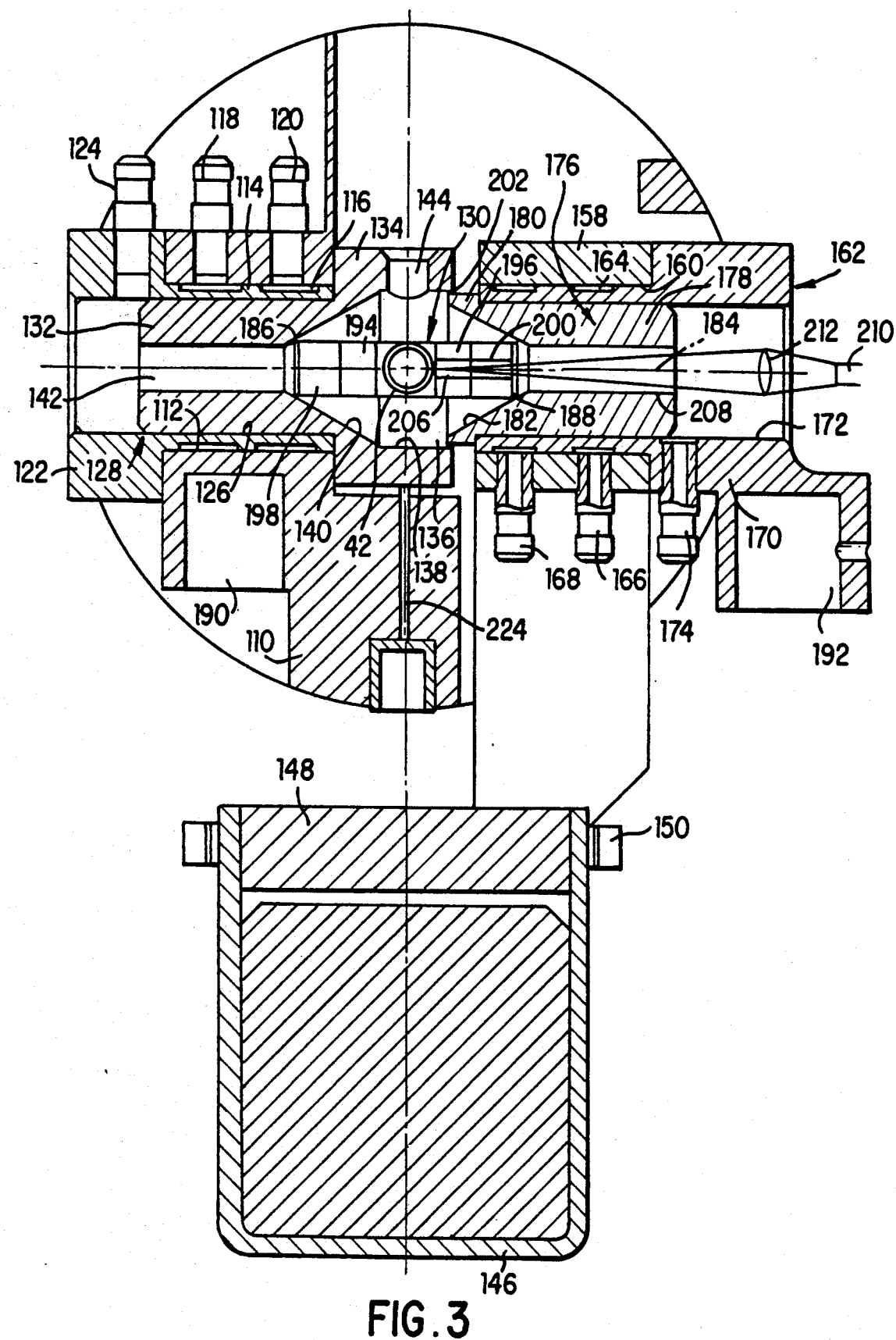
FIG. 3 shows a sectional view taken along the line III—III of FIG. 2.

The construction of the atomizing device with the solenoid 44 and the furnace is illustrated in detail in FIG. 2 and FIG. 3.

The solenoid 44 has a u-shaped magnetical return path 76 made of laminated iron and aligned pole pieces 46, 48. The pole pieces are cylindrical and are frustro conically tapered at the ends facing each other.

The pole pieces are made of a glued metal powder compound material. This material has favorable magnetic characteristics and is easy to be machined. The surface lines of the frustro conically shaped sections of the pole pieces 46, 48 form angles of 63° with the axes of the pole pieces. The opposite pole surfaces 47 and 49, respectively, are designed such that a saturation induction results in the area of the pole surfaces. In this way an optimum concentration of the magnetic field is effected. The angle of inclination of the pole pieces is selected such that the magnetic field remains as homogenous as possible.

The pole pieces 46 and 48 are arranged on the aligned end pieces 78 and 80, respectively, which are provided on the legs of the u-shaped magnetical return path 76 or yoke and project inwardly from there. The aligned bores 50 and 52 extend through the pole pieces 46 and 48, respectively, and the end pieces 78 and 80. The bores 50 and 52, respectively, are provided by conical inner surfaces in order to ensure focussing of the measuring light beam in the center of the furnace body 42 but thereby removing as few iron as possible. In the area of the ends pieces 78 and 80 the bores 50 and 52, respectively, form shoulders 82. Window holders 84 and 86, respectively, are inserted into the bores 50 and 52 and are sealed by O-rings 88. Windows 90 are located in the window holders 84 and 86 which are arranged oblique in the window holders 84 and 86, respectively, in order to avoid relfections, and which are held by sealing rings 92.

An integral element 94 made of a non-magnetic material as aluminum is provided on the pole pieces 46 and 48. This element forms the coil holder 56 and 58 on which the field coils 60 and 62, respectively, are wound, and on the other hand forms a contact carrier 96 which carries one of the contacts between which the furnace is held.

The coil holders 56 and 58 are formed by spool-shaped elements with two flanges 98 and 100 or 102 and 104, respectively, and hub portions 106 and 108, respectively. The hub portions 106 and 108 match the shape of the pole pieces 46 and 48, respectively, that means they have also conical sections 107 and 109, respectively, adjacent to an air gap, as well. A block 110 having a bore 112 is arranged between the flanges 100 and 102 facing each other of the two coil holders 56 and 58. An insert 114 is provided in the bore 112 and has u-shaped grooves 116 on its outer surface, these grooves together with the inner surface of the bore 112 forming a cooling passage. This cooling passage communicates with an inlet 118 and an outlet 120 for the cooling liquid. The insert has a head portion 122 whereon an inert gas inlet 124 is provided. A central axial bore 126 extends throughout the insert which is closed at its left end in FIG. 3. A contact 128 is provided in this axial bore, by which contact a furnace 130 for the electrothermal atomization is held on one side, and through which contact also the current supply for the furnace 130 is accomplished.

The contact 128 has a shaft 132 which is located in the axial bore 126, and a head 134. The head 134 has a recess 136 in its end face. First of all this recess 136 is cylindrical in a section 138 adjacent to the end face and then tapers conically in a section 140. A central axial bore 142 extends in the shaft 132 and ends on the bottom of the recess 136. A radial inlet port 144 is formed in the cylindrical section 138 in the head 134, on top in FIG. 3, and permits a sample to be introduced therethrough into the furnace.

The magnetic return path 76 of the solenoid 44 is surrounded by a sheet metal element 146 having a u-shaped cross-section in which a bearing element is held by a bolt 150. A pivotable arm 154 is pivotably mounted on a pin 152 of the bearing element 152 through a bearing bushing 156. A movable block 158 is provided at the pivotable arm 154. Similar to the block 110 the block 158 has a bore 160. An insert 162 similar to the insert 114 is arranged in the bore 160. The insert 162 has u-shaped grooves 164 on its outer surface, these grooves together with the inner surface of the bore 160 forming a cooling passage. This cooling passage communicates at its ends with an inlet port 166 and an outlet port 168 for the cooling liquid. The insert has a head 170. A central axial bore 172 extends through the insert 162 and the head 170. On the right side of FIG. 3 the axial bore 172 is closed by a window. An inert gas port 174 opens into the axial bore 172. A contact 176 is arranged in the axial bore 172. The contact 176 has a cylindrical shaft 178 and a flat head 180. A conical recess 182 is formed in the end face of the head 180. The recess corresponds approximately to the recess section 140. A central axial bore 184 similar to the bore 142, extends through the shaft 178 of the contact 176.

In operational position of the pivotable arm 154, as illustrated in FIG. 3, the furnace 130 is held between the contacts 128 and 176 with conical contact surfaces 186 and 188. Then the contacts 128 and 176 are aligned. The current is supplied to the furnace 130 through the blocks 110 and 158, the inserts 114 and 162 and the contacts 128 and 176. For this purpose the block 110 and the insert 162 are provided with plug-type connectors 190 and 192, respectively, for the high-current cables.

The furnace 130 contains the actual furnace body 42 which can be recognized best in FIG. 2. Diametrically opposite contact ribs 194 and 196 which can be seen in FIG. 3 extend along the furnace body 42. Substantially cylindrical contact pieces 198 and 200 are adjacent to the contact ribs 194 and 196, said contact pieces being held between the contacts 128 and 176 by the conical contact surfaces 186 and 188. The axes of the contact pieces 198 and 200 are aligned with the axes of the contacts 128 and 176 in the paper plane of FIG. 3 and extend perpendicular to the axis of the furnace body which is aligned with the measuring light beam 18. An inlet port is provided in the furnace body perpendicular to these two axes, that means on the top of FIG. 2 and FIG. 3, this inlet port being aligned with the inlet port 144 and permits sample to be introduced therethrough into the furnace 130.

The contacts 128 and 176 form a cavity with their recesses 136 and 168, this cavity containing the furnace 130. The contacts 128 and 176 are separated from each other only by a relatively narrow separating gap 202. The pivotable arm 154 can be deflected clockwise in FIG. 3 by a pneumatic tilting device (not illustrated). This is indicated in FIG. 3 by an arrow. Thereby the block 158 with the insert 162 and the contact 176 is deflected and the furnace 130 is accessible. In this way an exchange of the furnace 130 can be accomplished. An inert gas is supplied through the inert gas ports 124 and 174. This inert gas flows through the bores 126 and 172, respectively, and the axial bores 142 and 184, respectively, to the contact pieces 198 and 200, respectively, of the furnace 130. Then the inert gas is distributed in the furnace 130 by passages which still have to be described. The contacts 128 and 176 and the furnace 130 are made of graphite. The inert gas prevents the furnace 130 from getting into contact with air oxigen, when it is heated, and thus from burning.

A shielding disc 204 with a central aperture for the measuring light beam is arranged between the contact 128 and the end face of the pole piece 48 as can be seen in FIG. 2. The shielding disc 204 is made of pyrolytic plastic with a high heat conductivity in the plane of the shielding disc 204 and a low heat conductivity perpendicular to this plane. In this way the pole piece 48 is protected from high temperatures of the furnace 130 and the contact 128.

The axial bores 172 and 184 in the insert 162 and the contact 176 and the inert gas passage 206 in the contact piece 200 and the contact ledge 196 serve simultaniously for accommodating a pyrometer path of rays 208 in which a part of the wall of the furnace element 42 is observed by a radiation detector 210 by means of an imaging system 212. The signal of the radiation detector provides a measure of the temperature of the furnace element 42 and allows control of the furnace temperature.

As can be seen best in FIG. 2 the windings of the field coils 60 and 62 are made of a copper tubes 214 with a longitudinal passage 216 and an insulation 218. The copper tubes 214 have a relatively large cross-section for the electrical current. High currents are flowing with relatively few windings for generating the magnetic field. A cooling liquid is flowing through the longitudinal passage 216 and dissipates Joule's heat generated by the electrical current in the field coils 60 and 62 but also dissipates heat which is transmitted from the furnace 130 to the field coils. This makes it possible to arrange the field coils 60 and 62 on the pole pieces 46, 48 close to the furnace 130. The air gap is just as large as necessary for accomodating the length of the furnace body 42.

The windings of the field coils 60 and 62 are arranged in the area of the frustro conically tapering sections of the pole pieces 46 and 48 also in the circumferential recesses 220, and 47 and 49, respectively, having a v-shaped cross-section, formed between the flanges 100 and 102, respectively, and the frustro conical sections of the hub portions 106 and 108, respectively. Therefore the windings are preferably provided close to the pole surfaces 47 and 49, respectively, of the pole pieces 60 and 62, respectively. This counteracts the development of stray fields and promotes the homogeneousness of the magnetic field generated.

This is achieved by the compulsory cooling of the windings. The windings of the field coils 60 and 62 cool also the pole pieces 46 and 48, respectively and that just in the area of the pole surfaces 47 and 49, respectively, where the pole pieces are very close to the furnace 130.

As can be seen in FIG. 1 the cooling liquid is supplied through cooling liquid inlets 226 and is drained through cooling liquid outlets 228.

As can be seen in FIG. 3 the coil holders 56 and 58 and the contact carrier 96 are provided with a radial slot 224. These elements are made of a well heat conductive material as aluminum in order to ensure a good heat dissipation. Normally such well heat conductive materials are also well electrically conductive. Therefore the magnetic field can induce eddy currents in the coil holders 56, 58 and the contact carrier. In order to avoid this the elements are provided with a longitudinal slot as illustrated.

I claim:

1. Solenoid for generating a magnetic field at the location of a sample in an atomic absorption spectrometer, wherein a shift of the absorption lines of the atoms of the element looked for in the sample relative to the emission lines of this element in a measuring light beam passed through an atomized sample is caused by the magnetic field due to the Zeeman effect, comprising
   (a) a pair of pole pieces (46, 48) between which an air gap is formed, an atomizing device atomizing the sample within this air gap,
   (b) a magnetic return path (76) connecting the pole pieces (46, 48),
   (c) field coils (60, 62) for generating a magnetic flux through the pole pieces (46, 48), the air gap and the magnetic return path (76),
characterized in that
   (d) the field coils (60, 62) are arranged on the pole pieces (46, 48) close to the air gap, and
   (e) the windings of the field coils (60, 62) are formed by tubes through which a cooling liquid can be passed.

2. Solenoid as set forth in claim 1, characterized in that
   (a) the pole pieces (46, 48) are provided with aligned apertures (50, 52) for the passage of the measuring light beam (18),
   (b) a contact carrier is arranged on the pole pieces (48, 50), a contact the axis of which extends parallel to the axis of the measuring light beam (18) being supported in the contact carrier for holding a transversely heated furnace (130) for the electrothermal atomization of the sample in the air gap of the solenoid (44) and for the current supply to this furnace (130).

3. Solenoid as set forth in claim 2, characterized in that the contact carrier is integral with coil holders (56, 58) which carry the field coils (60, 62) and is attached to both pole pieces with the coil holders (56, 58).

4. Solenoid as set forth in claim 1, characterized in that the pole pieces (46, 48) are frustro conically tapered at their ends facing each other.

5. Solenoid as set forth in claim 4, characterized in that pole faces (47 and 49, respectively) formed by the frustro conical tapering correspond to saturation induction.

6. Solenoid is set forth in claim 4, characterized in that the surface lines of frustro-conically tapered sections of the pole pieces (46, 48) form an angle of 63° with the axes of the pole pieces.

7. Solenoid as set forth in claim 4, characterized in that
   (a) coil holders (56, 58) are attached to the pole pieces (46, 48) consisting of a hub portion (106, 108) matching the shape of the pole piece (46, 48) and of flanges (98, 100; 102, 104) projecting radially from the ends of the hub portion, and (b) the windings of the field coils (60, 62) are wound close to the pole surface (47 and 49, respectively) on the coil holders (106, 108) in the area of the frustro conically tapered sections.

8. Solenoid as set forth in claim 1, characterized in that the pole pieces (46, 48) are made of a glued metal powder compound material.

9. Solenoid as set forth in claim 1, characterized in that the windings of the field coils (60, 62) are wound on slotted coil holders (56, 58) and consist of heat conductive material.

* * * * *